United States Patent [19]

Polta

[11] Patent Number: 5,052,380

[45] Date of Patent: Oct. 1, 1991

[54] COLORED ORTHOPEDIC RESINS AND ORTHOPEDIC CASTING MATERIALS INCORPORATING SAME

[75] Inventor: Charles C. Polta, Roseville, Minn.

[73] Assignee: Minnesota Mining and Manufacturing Company, St. Paul, Minn.

[21] Appl. No.: 376,565

[22] Filed: Jul. 7, 1989

[51] Int. Cl.$^5$ ................ A61F 13/04; A61L 15/10; A61L 15/14

[52] U.S. Cl. ...................... 128/90; 427/342; 427/389.8; 428/253; 428/254; 428/255; 428/273; 428/425.6; 428/913

[58] Field of Search ............ 128/89 R, 89 A, 90, 128/82, 82.1; 428/253, 254, 255, 273, 542.8, 913; 427/342, 389.8

[56] References Cited

U.S. PATENT DOCUMENTS

| | | | |
|---|---|---|---|
| 3,908,644 | 9/1975 | Neinart et al. | 128/90 |
| 3,912,667 | 10/1975 | Spitzer et al. | 260/2.5 E |
| 3,955,566 | 5/1976 | Stoffey | 128/90 |
| 3,990,437 | 11/1976 | Boyden, Jr. et al. | 128/90 |
| 3,992,348 | 11/1976 | Jones et al. | 260/30.6 R |
| 3,994,835 | 11/1976 | Wolf et al. | 260/2.5 AM |
| 4,060,075 | 11/1977 | Blomer et al. | 128/90 |
| 4,105,025 | 8/1978 | Wang et al. | 128/90 |
| 4,113,721 | 9/1978 | Hauser et al. | 260/178 |
| 4,132,840 | 1/1979 | Hugl et al. | 521/167 |
| 4,135,015 | 1/1979 | Boyden et al. | 128/90 |
| 4,175,177 | 11/1979 | Potts | 528/354 |
| 4,231,356 | 11/1980 | Usukura | 128/90 |
| 4,238,522 | 12/1980 | Potts | 427/2 |
| 4,255,326 | 3/1981 | Giles et al. | 260/152 |
| 4,282,144 | 8/1981 | Weaver et al. | 260/152 |
| 4,284,729 | 8/1981 | Cross et al. | 521/158 |
| 4,286,586 | 9/1981 | Potts | 128/90 |
| 4,301,068 | 11/1981 | Giles et al. | 260/152 |
| 4,301,069 | 11/1981 | Weaver et al. | 260/152 |
| 4,335,158 | 6/1982 | Beede et al. | 427/2 |
| 4,376,438 | 3/1983 | Straube et al. | 128/90 |
| 4,404,333 | 9/1983 | Watanabe et al. | 525/437 |
| 4,411,262 | 10/1983 | von Bonin et al. | 128/90 |
| 4,442,833 | 4/1984 | Dahlen et al. | 128/90 |
| 4,483,332 | 11/1984 | Rind | 128/89 R |
| 4,502,479 | 3/1985 | Garwood et al. | 128/90 |
| 4,507,407 | 3/1985 | Kluger et al. | 521/113 |
| 4,512,340 | 4/1985 | Buck | 128/90 |
| 4,547,561 | 10/1985 | Wegner | 528/60 |
| 4,609,578 | 9/1986 | Reed | 428/76 |
| 4,652,493 | 3/1987 | Reichmann et al. | 128/90 X |
| 4,667,661 | 5/1987 | Scholz et al. | 128/90 |
| 4,676,234 | 6/1987 | Wegner et al. | 128/90 |
| 4,705,840 | 11/1987 | Buckanin | 528/53 |
| 4,751,254 | 6/1988 | Kluger et al. | 521/163 |
| 4,767,893 | 8/1988 | Ball et al. | 174/84 R |
| 4,774,937 | 10/1988 | Scholz et al. | 128/90 |
| 4,775,748 | 10/1988 | Kluger et al. | 534/729 |
| 4,784,123 | 11/1988 | Robeson | 128/90 |
| 4,912,174 | 3/1990 | Grouiller | 525/415 |
| 4,934,356 | 6/1990 | Klintworth, Jr. | 128/90 |

FOREIGN PATENT DOCUMENTS 2334169 1/1974 Fed. Rep. of Germany .
1394365 5/1975 United Kingdom .
1583377 1/1981 United Kingdom .

OTHER PUBLICATIONS

Reactint ® Urethane Colorants Product Literature of Milliken Chemicals, (7 pages).
"Orasol ® Solvent Soluble Dyes," A Product Brochure of Ciba-Geigy Corporation.
S. H. Bates et al., "The Advantages of a Color System for Polyurethanes Using Polyol-Bound Colorants," Polyurethane World Congress 1987, pp. 916-920.

Primary Examiner—Robert A. Hafer
Assistant Examiner—Kevin G. Rooney
Attorney, Agent, or Firm—Gary L. Griswold; Walter N. Kirn; Dale E. Hulse

[57] ABSTRACT

The present invention relates to colored orthipedic resins and colored orthopedic casting materials which are storage stable. In making the colored orthopedic resins and colored orthopedic casting materials, a chromophore-containing polyol is covalently bonded into a prepolymer resin.

15 Claims, No Drawings

COLORED ORTHOPEDIC RESINS AND ORTHOPEDIC CASTING MATERIALS INCORPORATING SAME

BACKGROUND

1. Field of the Invention

The present invention relates to colored orthopedic resins and colored orthopedic casting materials which are storage stable.

2. The Prior Art

Recently, water curable, isocyanate functional, polyurethane prepolymers have been found to be extremely useful in formulating a resin for orthopedic casting materials, as disclosed, for example, in U.S. Pat. No. 4,502,479 (Garwood et al.), U.S. Pat. No. 4,609,578 (Reed), U.S. Pat. No. 4,667,661 (Scholz et al.), and U.S. Pat. No. 4,774,937 (Scholz et al.). Most commonly, a knitted fiberglass fabric is used as the scrim onto which such polyurethane prepolymers are coated To initiate the cure of such water curable orthopedic casting materials, the material is contacted with water, typically by immersing a roll of the material in water. Upon immersion, the curing process begins as the isocyanate functional groups begin polymerizing in the presence of water Such polymerization is often aided or controlled by the use of a catalyst, such as is disclosed, for example, in U.S. Pat. No. 4,705,840 (Buckanin). Since these water curable orthopedic casting materials must be stored in moisture-proof pouches or containers for significant periods of time before use, storage stability is a significant concern.

Quite recently, colored orthopedic casting materials have become desirable from the standpoint of aesthetic appeal to the wearer. Unfortunately, some problems have been experienced with early attempts to provide colored orthopedic casting materials For example, faded or splotchy color, leaching of the color from the materials, and colored water drips have been experienced.

As will thus be appreciated, there are many obstacles to successfully coloring an orthopedic casting material for aesthetic appeal. Two different types of colorants have historically been used when attempting to provide a desired color to a material: dyes and pigments Dyes are typically soluble in the system to be colored, whereas pigments typically are not.

Hence, one of the problems involved in providing a colored orthopedic resin or colored orthopedic casting material is the difficulty in mixing the dyes or pigments into the polymeric mixture which will form the resin. Since pigments are typically dry powders at room temperature, relatively long periods of time are required o attempt to mix and disperse the pigment powder evenly throughout the polymeric mixture, and often a millbase must be prepared as a vehicle for pigment addition Dyes generally need to be dissolved into the polymeric mixture to provide effective color; again, uniform dispersion or dissolution of the dye is often very difficult to achieve and mixing requires a relatively long period of time. Hence, relatively long mixing times and the inability to uniformly disperse the pigment or dye throughout the polymeric mixture can often be a problem.

Stability of the color in the resultant colored polymeric material is also a problem. Over time, both pigments and incompletely dissolved dyes tend to settle out, thus resulting in a color concentration gradient within the polymeric material and resulting in a nonuniform coloring. In this regard, dark splotches of the dye or pigment are sometimes formed, resulting in a rather nonuniform color pattern. The problem of color stability in a colored orthopedic casting material may be further aggravated by the presence of the catalyst used to control the cure time. Since such catalysts are relatively powerful chemical agents, they can also adversely affect the stability of the color, for example, causing the color to break down and fade over time.

Another problem is related to resin stability, namely, the incompatibility of the various colorants and the components of the resin. Because dyes and pigments are chemically quite dissimilar to the components used to form the resin of an orthopedic casting material, the properties of the resin may be adversely affected. For example, some dyes and pigments have been found to catalyze or participate in unwanted reactions which tend to accelerate the increase in resin viscosity over time. Excessive increases in viscosity can render a resin-impregnated casting material unuseable.

Another problem which must be overcome in providing a colored orthopedic resin or casting material is the tendency of the dye or pigment to leach or bleed from the resin or material once formed. Unfortunately, dyes can leach from a polymeric material and pigments can migrate from a polymeric material under certain conditions. Related to this is the problem of a colored drip which may be experienced with polymeric materials containing a pigment or dye which are activated by water to initiate cure. If the color leaches or migrates from the resin upon contact with the water, a messy and very undesirable color drip may result.

Additional concerns with respect to the use of dyes or pigments to color polymeric materials are safety and cleanliness. Many dyes are considered toxic to humans. Dry pigment powders can pose a safety problem from the standpoint of inhalation of the powder Since dyes stain many materials with which they come in contact and since pigment powders can be very messy to handle, maintaining a clean environment can also be a problem when using dyes and pigments.

In the art of producing cured urethane foams, "reactive colorants" have been proposed. In this regard, U.S. Pat. No. 4,775,748 (Kluger et al.), U.S. Pat. No. 4,751,254 (Kluger et al.), and U.S. Pat. No. 4,507,407 (Kluger et al.), which three patents are incorporated herein by reference, disclose reactive colorants and processes for the in situ coloration of thermosetting resins. There is no suggestion in any of those patents that the reactive colorants disclosed could be used in an isocyanate functional, polyurethane prepolymer for orthopedic use.

From the foregoing, it will be appreciated that what is needed in the orthopedic art are colored orthopedic resins and colored orthopedic casting materials wherein the colorant: (1) can be mixed into the prepolymer resin mixture with relative ease and in a relatively short period of time; (2) does not settle out of the prepolymer resin, but rather provides for a very uniform color, even after being stored for significant periods of time; (3) is compatible with the components of the prepolymer resin so as to not adversely affect the resin such as by accelerating the increase in the viscosity of the resin when stored over time; (4) does not leach, migrate, or bleed from the prepolymer resin during storage, during cure, or after cure; and (5) is relatively nontoxic and does not present a significant safety hazard or cleanliness problem. Such colored orthopedic resins and colored orthopedic casting materials made from the same are disclosed and claimed herein.

BRIEF SUMMARY AND OBJECTS OF THE INVENTION

The present invention relates to colored orthopedic resins and colored orthopedic casting materials made therefrom which exhibit greatly improved storage stability and other characteristics.

The preferred resins of the present invention are water curable, isocyanate functional, polyurethane prepolymer resins which are formed by the reaction of a polyol with an excess of a polyisocyanate. (An excess of the polyisocyanate is employed in formulating the prepolymer such that the resultant prepolymer is isocyanate functional, and is therefore capable of curing to a thermoset state upon contact with water.) When used in an orthopedic casting material in accordance with the present invention, the colored orthopedic resin is coated onto a suitable scrim. Although many scrims are known for such a purpose, it is presently preferred to employ a knitted fiberglass fabric as the scrim material.

The colored orthopedic resins and colored orthopedic casting materials of the present invention are achieved by the use of a chromophore-containing polyol (also referred to as a "reactive colorant") which comprises at least a portion of the total polyol employed in formulating the resin. The chromophore-containing polyols or reactive colorants used to formulate the colored resins and colored orthopedic casting materials of the present invention react with the polyisocyanate so as to become covalently bound to the resultant polyurethane prepolymer.

The reactive colorants of the present invention are thus simply mixed into the prepolymer itself or into the prepolymer reaction mixture so as to react and become bound into the prepolymer. Advantageously, the reactive colorants of the present invention are readily miscible with most polyurethane prepolymer components, and the amount of time required to mix the reactive colorants of the present invention into the prepolymer reaction mixture is surprisingly small. The ease of mixing the reactive colorants of the present invention into the prepolymer resin mixture is further facilitated by the fact that the preferable reactive colorants of the present invention are liquids at room temperature. Hence, the dispersibility problems, health and safety problems, and cleanliness problems related with powders such as the pigment powders of the prior art are substantially avoided.

Because the reactive colorants of the present invention are bound directly into the backbone of the polyurethane prepolymer, the colored orthopedic resins and colored orthopedic casting materials of the present invention are surprisingly color stable over time. In this regard, since the reactive colorants are directly bound into the polyurethane prepolymer, no significant settling or migration of the reactive colorants is experienced, and excellent uniformity of the color in the colored resins is achieved and does not substantially change after about 5 weeks of aging at 120° F. (49° C.). Thus, the present invention solves the problems of incompletely dissolved dyes, poorly mixed pigments, or pigments or dyes which settle with time, thereby avoiding nonuniform color problems Surprisingly, when using the chromophore-containing polyols or reactive colorants of the present invention, the presence of such chromophore-containing polyols does not cause a significantly higher rate of increase in the viscosity of the colored orthopedic resin over time as compared to noncolored orthopedic resins. In this regard, it is believed that by introducing color into the resin or orthopedic casting material by using a polyol containing a chromophore, the chromophore function of the colorant is much less likely to adversely affect the other components of the prepolymer resin because of the fact that it is linked to a polyol, and polyols are normally employed in forming the prepolymer resin.

Quite advantageously, because the reactive colorants of the present invention are covalently bound to the polyurethane prepolymer, the problem of color leaching, migration, or bleeding from the resin is substantially avoided. Further in this regard, significantly no colored water drip has been experienced with the colored resins or colored orthopedic casting materials of the present invention when activated by water to initiate cure. Additionally, fading of the color in the orthopedic casting materials is substantially avoided during storage.

Also advantageously, the reactive colorants of the present invention are relatively nontoxic and nonhazardous, and can be easily cleaned up with soap and water if spilled. In this regard, there are no presently known toxic effects when the colored resins and colored orthopedic casting materials of the present invention are contacted by the skin of the person applying the same or the skin of the patient.

It is, therefore, an object of the present invention to provide colored orthopedic resins and colored orthopedic casting materials employing chromophore-containing polyols or reactive colorants which can be mixed into a prepolymer reaction mixture with relative ease over a relatively short period of time.

Another object of the present invention is to provide colored orthopedic resins and colored orthopedic casting materials which are relatively color stable, experiencing surprising uniformity of color over a substantial period of storage time.

A further object of the present invention is to provide colored orthopedic resins and colored orthopedic casting materials employing reactive colorants which are chemically similar to polyols typically used in polyurethane prepolymer resins for orthopedic use, thereby substantially avoiding adverse reactions between the reactive colorants and the prepolymer resin, such as the undesirable acceleration of viscosity increase in the resin during storage.

Still another object of the present invention is to provide colored orthopedic resins and colored orthopedic casting materials where leaching or migration of the color from the resins is substantially avoided.

Yet another object of the present invention is to provide colored orthopedic resins and colored orthopedic casting materials employing colorants which are relatively safe and can be easily cleaned up if spilled.

These and other objects and features of the present invention will become more fully apparent from the following description and appended claims.

DETAILED DESCRIPTION OF THE PREFERRED EMBODIMENTS

The present invention relates to colored resins and colored resin-coated materials which are storage stable and have other benefits as outlined herein. These colored resins and colored resin-coated materials have particular utility when used in orthopedic casting applications, however, such is not their only utility. Hence, although the following discussion of the colored resins and colored resin-coated materials of the present invention is set forth in the context of an orthopedic casting material application, it will be appreciated that the applications and uses of the colored resins and colored resin-materials of the present invention are not so limited. For example, such colored resins and colored resin-coated materials could be used in nonorthopedic applications as a protective material to protect the surface of an article or structure from abrasion or corrosion or as a material for reinforcing, sealing, or repairing the surface of an article or structure requiring such.

The curable resins which are provided with a color in accordance with the present invention are water activated, or preferably, water curable resins. In this regard, water curable, isocyanate functional, polyurethane prepolymers are presently preferred.

Presently preferred resins for use in the present invention include those disclosed in U.S. Pat. No. 4,667,661 (Scholz et al.) and U.S. Pat. No. 4,774,937 (Scholz et al.) which patents are incorporated herein by reference. The polyurethane prepolymer resins disclosed in these patents are formed by the reaction of a polyol with a polyisocyanate. The resins disclosed in the two aforementioned patents also include tack reducing agents which facilitate application of the orthopedic casting materials. However, in the present invention, these resins are modified by using a polyol (which represents at least a part of the total polyol concentration employed) having a chromophore attached thereto. Such chromophore-containing polyols or reactive colorants become covalently bonded into the polyurethane prepolymer resin and serve to impart a desired color to the resin or orthopedic casting material made therefrom.

Thus, the reactive colorants of the present invention are chromophores which are bonded to polyols. Presently preferred reactive colorants include dyestuffs which are covalently bound to either polyether or polyester polyols.

Several reactive colorants which are polyether polyols with bonded dyestuffs are presently preferred and may be commercially obtained. Included in this category of preferred reactive colorants are the Reactint ® polyols available from Milliken Research Corporation, Inman, S.C. Reactint ® polyols which have been successfully employed in the present invention include Reactint ® Black X40LV, Reactint ® Blue X3LV, Reactint ® Orange X38, Reactint ® Red X52, Reactint ® Violet X80, and Reactint$^R$ Yellow X15. Each of the foregoing Reactint ® polyols are polyether polyols having a dyestuff covalently bonded thereto, and all are liquids at room temperature.

The order of mixing the reactive colorant or colorants with the various ingredients which go into the prepolymer resin does not appear to be critical, as long as the reactive colorant is uniformly dispersed during mixing. Advantageously, mixing the reactive colorants of the present invention with the prepolymer resin mixture is achieved with relative ease and in a short period of time. The reactive colorants of the present invention provide colored resins which are color stable and non-settling at the relatively high temperatures (about 100° F. or 38° C.) at which the prepolymer resins are generally stored before being coated onto a suitable scrim for use as an orthopedic casting material. The resultant colored casting material is then stored in a moisture-free pouch or container, under which conditions the colored casting material again is extremely color stable. The color of the colored resin-coated materials of the present invention remains stable through the period of removing the casting material from the pouch, activating the material by dipping it in water, and allowing the material to cure.

Although the amount of chromophore-containing polyol or reactive colorant employed in a particular prepolymer resin will vary according to the type, shade, and intensity of the color desired, typically the reactive colorants comprise from about 0.01% to about 2% by weight of the total resin, more preferably from about 0.05% to about 1.5% by weight of the resin.

As is evidenced by the appended examples, the reactive colorants of the present invention provide a colored resin which is storage stable in the sense that substantially no colorant settling occurs and the uniformity of color is quite good and remains substantially unchanged after about 5 weeks of aging at 120° F. (49° C.). Further, the colored resins are storage stable in the sense that the presence of the reactive colorant does not cause a significantly higher rate of viscosity increase in the colored resin over time as compared to noncolored resins. In addition, the leaching or migration of colorant from the colored resins of the present invention is virtually nonexistent.

As mentioned, the curable resins of the present invention are formed, for example, in accordance with the teachings of U.S. Pat. No. 4,667,661 and U.S. Pat. No. 4,774,937, with the modification that a chromophore-containing polyol as disclosed herein is also employed. It may also be desirable to vary the proportions of the ingredients in the resin somewhat from the teachings of U.S. Pat. Nos. 4,667,661 and 4,774,937 when using chromophore-containing polyols in accordance with the present invention. For example, to offset the hydroxy functionality of the polyol colorants, additional isocyanate could be added. This would be desirable if the colorant concentration were high enough to make a significant difference in the NCO:OH ratio of the resin.

Preferably, the NCO:OH ratio of the polyisocyante/polyol reactants is about 1.2:1 to 4.5:1, and most preferably is about 1.8:1 to 3.8:1. In addition, as set forth in U.S. Pat. No. 4,667,661 and U.S. Pat. No. 4,774,937, the curable resins of the present invention are considered fluids or liquids, and in this regard, have viscosities as set forth hereinbelow.

In choosing the relative proportions of the resin ingredients for purposes of the present invention, the following criteria should be kept in mind: 1) proper ring strength and ring delamination strength of the resultant cast should be preserved by ensuring sufficient resin content, while at the same time preserving adequate porosity; 2) the viscosity of the resin should be kept within a range that enables the colored resin-coated casting material to be easily unwound and applied to the patient, generally within the range of 10,000 to 300,000 centipoise when measured on a Brookfield RVT Viscometer using spindle #6, more preferably within the range of 10,000 to 100,000 centipoise, and most preferably within the range of 10,000 to 80,000 centipoise; 3) the set time of the material should be from about 2 to about 18 minutes, more preferably from about 2.5 to about 10 minutes, and most preferably from about 3 to about 5 minutes.

In accordance with the teachings of U.S. Pat. Nos. 4,667,661 and 4,774,937, the curable resins used in the present invention are polymerizable to a thermoset state. The resin is preferably nontoxic in the sense that it does not give off significant amounts of toxic vapors during curing which may be harmful to either the patient or the person applying the orthopedic casting material, and also in the sense that it does not cause skin irritation either by chemical irritation or by the generation of excessive heat during cure. Furthermore, the resin must be sufficiently reactive with the curing agent (e.g., water) to ensure rapid hardening of the orthopedic casting material once it has been applied, but not so reactive that it does not allow for sufficient working time to apply and shape the orthopedic cast or splint. Initially, the orthopedic casting material must be pliable and conformable and should adhere to itself. Then in a short time following the completion of application, it should become rigid, or at least semirigid, and strong enough to support the loads and stresses to which the cast or splint is subjected by the activities of the wearer. Thus, the orthopedic casting material must undergo a change of state from a flexible condition to a relatively rigid condition in a matter of minutes.

As mentioned, presently preferred resins used in the present invention are water curable, isocyanate functional, polyurethane prepolymer resins. These resins are formed by reacting a polyol with an excess of a suitable polyisocyanate. By using an excess of polyisocyanate, the resultant prepolymer contains unreacted isocyanate groups which provide for the water curability of the material at a later date when the material is to be applied as an orthopedic material. At least a portion of the total amount of polyol employed is a chromophore-containing polyol as disclosed herein. However, in many of the preferred embodiments of the present invention, the total polyol concentration is represented by polyols which are both colored and noncolored. Indeed, such a "blend" of colored polyols and noncolored polyols is presently preferred in most embodiments. In this regard, the color intensity of the preferred colorants is such that only a relatively small proportion of the total polyol concentration is represented by the polyol colorants.

Conventional uncolored polyols which may be used as part of the total polyol concentration in forming the polyurethane prepolymers of the present invention include polypropylene ether glycols (available from Union Carbide, Danbury, Conn. as Niax TM PPG and from BASF Wyandotte Corp., Parsippany, N.J. as Pluracol TM P), polybutylene ether glycols (available from Dow Chemical, Midland, Mich. as XAS 10961.00 experimental polyol) polytetramethylene ether glycols (available from Quaker Chemical Company, Conshohocken, Pa. as Polymeg TM), polycaprolactone diols (available from Union Carbide as the Niax TM PCP series of polyols), and polyester polyols (hydroxyl terminated polyesters obtained from the esterification of dicarboxylic acids and diols such as the Lexorez TM polyols available from Inolex Corp., Chemical Division, Philadelphia, Pa.). As will be appreciated by those skilled in the art, the rigidity of the cured resin can be reduced by increasing the molecular weight of the polyols employed, or conversely, the rigidity can be increased by using lower molecular weight polyols.

It will be understood that, as used herein, the term "polyol" also includes virtually any functional compound having active hydrogen in accordance with the well-known Zerevitinov test, as described, for example, in *Chemistry of Organic Compounds* by Carl R. Noller, Chapter 6, pp. 121-122 (1957). Thus, for example, thiols and polyamines could also be used as "polyols" in the present invention, and the term "polyols" will be considered to include such other active hydrogen compounds.

In choosing an appropriate polyisocyanate, it is presently preferred to use an isocyanate which has a relatively low volatility, such as diphenylmethane diisocyanate (MDI), rather than a more volatile material such as toluene diisocyanate (TDI), which is also more toxic. Presently preferred isocyanates include 4,4'-diphenylmethane diisocyanate, 2,4'-diphenylmethane diisocyanate, and mixtures of these isomers together with possible small quantities of 2,2'-diphenylmethane diisocyanate (typical of commercially available diphenylmethane diisocyanate). However, isocyanates such as aromatic polyisocyanates and their mixtures which are derived from phosgenation of the condensation product of aniline and formaldehyde may also be used.

One example of a presently preferred resin which may be used in the present invention involves the reaction of an isocyanate known as Isonate TM 2143L (formerly known as Isonate 143L, a mixture containing about 73% MDI) which is available from the Dow Chemical Company, Midland, Mich. with a mixture of polypropylene oxide polyols which are available from Union Carbide and are known as Niax TM PPG 2025 and Niax TM LG-650, in addition to one or more of the chromophore-containing polyols disclosed herein. To prolong the shelf life of the resin, it is also preferable to include from about 0.01% to about 1% by weight of benzoyl chloride or other suitable stabilizer.

The reactivity of the curable resin, once it is exposed to the water, can be controlled by the use of a proper catalyst. The reactivity must not be so great that: (1) a hard film quickly forms on the resin surface preventing further penetration of the water into the bulk of the resin, or (2) the cast or splint becomes rigid before the application and shaping thereof has been completed. To produce suitable orthopedic casts and splints in accordance with the present invention, a set time of from about 2 to about 18 minutes following activation of the curable resin is preferred, with a more preferable set time being from about 2.5 to about 10 minutes, and a most preferable set time being from about 3 to about 5 minutes. Thus, the curable resins of the present invention also preferably contain a catalyst to control the set time and cure time of the resin.

Suitable catalysts for moisture curing polyurethane prepolymer resin systems are well known. For example, tertiary amine catalysts such as 4-[2-[1-methyl2-(4-morpholinyl)ethoxy]ethyl]morpholine (MEMPE) described in commonly assigned, U.S. Pat. No. 4,705,840 (Buckanin), in amounts ranging from about 0.5% to about 5% by weight of the resin system, may be used for this purpose. The MEMPE catalyst disclosed in U.S. Pat. No. 4,705,840, which patent is incorporated herein by reference, is the presently preferred catalyst system for use in connection with the present invention.

As mentioned, it is also preferred to make the curable resin of the present invention less tacky in accordance with the invention described in commonly assigned, U.S. Pat. No. 4,667,661 (Scholz et al.) and U.S. Pat. No. 4,774,937 (Scholz et al.). Reduced tackiness may be achieved by a number of means as described in U.S. Pat. No. 4,667,661 and U.S. Pat. No. 4,774,937. One technique for achieving such tack reduction is to lightly coat the surfaces of the resin-coated scrim with a mixture of a polydimethylsiloxane, having a viscosity of at least about 100 centistokes, and polyethylene oxide long chain aliphatic hydrocarbon waxes. Alternatively, a small amount of a polyethylene oxide—polypropylene oxide block copolymer (such as Pluronic F-108 available from BASF Wyandotte) may be added to the resin during prepolymer preparation, after which the polydimethylsiloxane may be applied onto the surface of the orthopedic article as before. The polydimethylsiloxane reduces resin tackiness prior to contact with water. The hydrophilic polyethylene oxide materials provide additional tack reduction upon contact with water.

If desired, the resins of the aforementioned Scholz et al. patents may be modified somewhat by the use of a polyol containing a stable dispersion of hydrophobic polymeric particles which serve to reduce foaming during cure. Curable resins incorporating such polymeric particles are disclosed in U.S. patent application Ser. No. 07/376,421, filed on the same date as the present application, filed in the names of Charles C. Polta and Matthew T. Scholz under Express Mailing Certificate No. B75869802, and entitled "Curable Resins with Reduced Foaming Characteristics and Articles Incorporating Same"; such patent application is incorporated herein by reference.

As disclosed in the aforementioned concurrently filed patent application, preferable polyurethane prepolymer resins are prepared by reacting a polyisocyanate with a polyol having polymeric particles dispersed therein which serve to reduce foaming during cure and provide other benefits. Preferably, such polymeric particles are made from hydrophobic vinyl monomers. However, any monomers may be employed which will form polymeric particles that act to significantly reduce foaming. Polymeric particles which have been found suitable for this purpose include polyacrylonitrile, a copolymer of acrylonitrile and styrene, and polyurea (formed, for example, from toluene diisocyanate and ethylenediamine). Polymeric particles made from epoxy based resins or combinations of any of the foregoing would also be suitable.

Several polyols are commercially available which already have such polymeric particles dispersed therein, and are thus suitable for practicing the invention. For example, Niax E-562 polyol (available from Union Carbide Corporation, Wheeling, West Virginia) which contains polymeric particles made of a copolymer of acrylonitrile and styrene (in a 50/50 weight % ratio); Niax E-701 polyol (also available from Union Carbide Corporation) which contains polymeric particles made of polyacrylonitrile; and Multranol 9151 polyol (available from Mobay Chemical Corporation, Pittsburgh, Pa.) which contains polymeric particles made of a polyurea; have been found to be useful in practicing the present invention. The presently most preferred polyols having polymeric particles dispersed therein are the aforementioned Niax E-562 and Niax E-701 polyols, which are referred to by Union Carbide Corporation as "Niax Performance Polyether Polymer Polyols."

Preferably, the polyols contain polymeric particles having an average diameter of less than about 20 microns. Preferably, the average diameter of the polymeric particles is greater than about 0.01 micron. At present, the polymeric particles more preferably have an average diameter of from about 0.01 microns to about 10 microns, and most preferably from about 0.3 microns to about 5 microns. However, there apparently is no minimum average diameter of particle needed to achieve the benefits of the invention, and it is believed that smaller particle sizes work best. Although polymeric particle sizes greater than the foregoing may be employed, it is believed that some of the benefits of the polymeric particles may be sacrificed if the particle sizes are too high.

Moreover, in the commercially available polymeric particle-containing polyols mentioned herein, the polymeric particles comprise from about 20% to about 38% by weight of the polyol. It is believed that polyols containing 10% to 45% by weight function adequately. When incorporating such polymeric particle containing polyols into the curable resins of the present invention, the polymeric particles preferably comprise from about 0.5% to about 10% by weight of the resin, more preferably from about 1% to about 6% by weight of the resin, and most preferably from about 2% to about 4% by weight of the resin.

Foaming of the resin-impregnated material (upon immersion in water) which would reduce the porosity of the cured material and its overall strength can also be minimized by using a foam suppressor such as DB-100 silicone fluid (Dow Corning) (now believed to be available under a new name, namely, Dow Corning Antifoam 1400), silicone Antifoam A (Dow Corning, Midland, Mich.), or silicone surfactant L550 or L5303 (available from Union Carbide) to the resin. It is presently preferred to use the Dow Corning DB-100 silicone fluid (or Dow Corning Antifoam 1400) at a concentration of about 0.1% to about 1% by weight of the resin.

The preparation of the orthopedic casting materials of the present invention generally involves the simple coating of the curable resin onto the fabric scrim. Generally, the scrim should be resin loaded to the point where the resin represents from about 35% to about 80% by weight of the total weight of the resin-coated scrim. In the case of a fiberglass scrim, the resin preferably represents from about 35% to about 60% by weight of the total weight of the resin-coated scrim, and preferably from about 38% to about 45% by weight. Manual or mechanical manipulation of the resin (such as by a nip roller or wiper blade) into the scrim is usually not necessary. However, some manipulation of the resin into the fabric may sometimes be desirable. Care should be given not to stretch the fabric scrim during resin coating, however, so as to preserve the stretchability of the material for its later application around the desired body part.

The curable resins of the present invention may be coated onto a variety of well-known flexible scrims for use as orthopedic casting materials or for other applications. Although many materials are well known for this purpose, fiberglass is presently preferred. In this regard, in one presently preferred embodiment of the present invention, the scrim comprises an extensible, heat-set, knitted fiberglass fabric as set forth in U.S. Pat. No. 4,609,578 (Reed), which patent is incorporated herein by reference. One example of a knitted fiberglass scrim which is within the scope of U.S. Pat. No. 4,609,578 is known by 3M, St. Paul, Minn., as the Scotchcast ® 2 knitted fiberglass scrim. The Scotchcast ® 2 scrim is used in the manufacture of 3M's Scotchcast ® 2 and Scotchcast ® Plus orthopedic casting materials.

If desired, a series of projections may also be formed along such a knitted fiberglass scrim in order to enhance the lamination properties thereof. A detailed description of scrims having such projections and the enhanced lamination achieved thereby is disclosed in U.S. patent application Ser. No. 07/376,873, filed on the same date as the present application, filed in the names of Matthew T. Scholz, Robert L. Assell, Ralph A. Wilkens, and Charles E. Alexson, under Express Mailing Certificate No. B75869812, and entitled "Orthopedic Casting Materials Having Superior Lamination Characteristics and Methods for Preparing Same"; such patent application is incorporated herein by reference. Such projections can be formed by abrading the scrim with, for example, a knurled roller, a knife edge, sharp or blunt teeth, or by other techniques.

As disclosed in the aforementioned concurrently filed patent application, a projection is considered to be a filament bundle which serves to enhance lamination and typically has 8 or more filaments per bundle. As further set forth in that concurrently filed patent application, the fabric scrims preferably have from about 75 to about 1,500 projections per gram of fabric scrim on the average, more preferably from about 100 to about 1,000 projections per gram of fabric scrim, and most preferably from about 300 to about 700 projections per gram of fabric scrim.

Orthopedic casting materials prepared in accordance with the present invention are applied to humans or other animals in the same fashion as other known orthopedic casting materials. First, the body member or part to be immobilized is preferably covered with a conventional cast padding and/or stockinet to protect the body part. Next, the curable resin is activated by dipping the orthopedic casting material in water. Excess water may then be squeezed out of the orthopedic casting material, and the material is wrapped or otherwise positioned around the body part so as to properly conform thereto. Preferably, the material is then molded and smoothed to form the best fit possible and to properly secure the body part in the desired position. Although often not necessary, if desired, the orthopedic casting material may be held in place during cure by wrapping an elastic bandage or other securing means around the curing orthopedic casting material. When curing is complete, the body part is properly immobilized within the orthopedic cast or splint which is formed.

The following examples are given for purpose of illustration only, and should not be considered comprehensive or restrictive.

EXAMPLES 1-7

In these Examples 1-7, colored resins incorporating chromophore-containing polyols were prepared in accordance with the present invention.

First, a 3200 pound (1455 kg) batch of a water curable, isocyanate functional, polyurethane prepolymer resin was prepared under dry conditions and constant agitation by adding the following chemical ingredients listed in Table I below in the proportions indicated therein.

TABLE I

| Ingredient | Weight % |
| --- | --- |
| Isonate 143L isocyanate (Dow Chemical) | 56.22 |
| MEMPE catalyst (From U.S. Pat. No. 4,705,840) | 1.32 |
| Pluronic F-108 polyethylene oxide-polypropylene oxide block copolymer (BASF Wyandotte Corp.) | 4.00 |
| DB-100 silicone fluid (Dow Corning) | 0.18 |
| Benzoyl chloride | 0.05 |
| Ionol ® butylated hydroxytoluene (BHT) (Shell Chemical) | 0.48 |
| PPG-425 polyol (Union Carbide) | 12.75 |
| PPG-725 polyol (Union Carbide) | 25.00 |

The exotherm created by the reactive ingredients raised the temperature within the reaction vessel from about 45° C. to about 60° C. during the procedure. After all ingredients had been included in the reaction mixture, the resultant resin was allowed to cool to about 27°–38° C.

In each of Examples 1-7, a 130 pound (59 kg) sample of colored resin was prepared. For each of Examples 1-7, a quantity of prepolymer resin from the resin batch of Table I above was mixed with the colorant or colorants set forth in Table II below, using the resin and colorant amounts set forth in Table II. This mixing was achieved by constant agitation of the prepolymer resin and colorant (or colorants) in a mixing vessel for at least about 45 minutes, such that the reactive colorant or colorants was uniformly mixed into the prepolymer resin by visual observation.

The resultant resin color obtained in each of Examples 1-7 is set forth in Table II below. Note that the weight percents set forth for the reactive colorants in Table II below are given as weight percent of the total final colored resin weight. As will be recognized, each of the reactive colorants used in Examples 1-7 were Reactint ® colorants available from Milliken Research Corporation. Table II also sets forth the weight ratios used where more than one reactive colorant was employed.

TABLE II

| Example | Reactive Colorant | Resin Weight (lb) | Reactive Colorant Weight (lb) | Reactive Colorant Weight % (% of total colored resin wt) | Resin Color Obtained |
| --- | --- | --- | --- | --- | --- |
| 1 | Reactint ® Black X40LV | 128.05 | 1.95 | 1.5 | Black |
| 2 | Reactints ® Yellow X15/Orange X38 (91.5/8.5 weight % ratio) | 129.61 | 0.39 | 0.3 | Golden Yellow |
| 3 | Reactint ® Black X40LV | 129.61 | 0.39 | 0.3 | Grey |
| 4 | Reactints ® Red X52/Yellow X15/Blue X3LV/Violet X80 (69.4/18.5/6.5/5.6 weight % ratio) | 128.70 | 1.30 | 1.0 | Maroon |
| 5 | Reactints ® Orange X38/Yellow X15 (53.1/46.9 weight % ratio) | 129.61 | 0.39 | 0.3 | Orange |
| 6 | Reactints ® Yellow X15/Orange X 38/Violet X80 (61.2/27.9/10.9 weight % ratio) | 129.87 | 0.13 | 0.1 | Tan |
| 7 | Reactints ® Violet X80/Red X52 (50/50 weight % ratio) | 129.61 | 0.39 | 0.3 | Purple |

The colored resin obtained in each of Examples 1-7 exhibited very uniform color, and no colorant settling was visually observed.

EXAMPLES 8-14

In these Examples 8-14, colored orthopedic casting materials were made using the colored resins prepared in Examples 1-7, respectively.

In each of Examples 8-14, the respective colored prepolymer resin was coated along a highly extensible, heat-set, knitted fiberglass fabric roll (known as the Scotchcast® 2 knitted fiberglass scrim) which was 3 inches (7.62 cm) wide and 675 feet (206 meters) long. Each colored resin was applied at a coating weight of about 42.5% resin, and each 675 foot roll was then converted into 4 yard (3.66 meter) rolls which were wound around 0.75 inch (1.91 cm) diameter polyethylene cores and stored in moisture-proof pouches.

Even after about 8 months of aging in the pouch, upon removal, the color in each of the orthopedic casting materials of Examples 8-14 was still very uniform and substantially unchanged. Moreover, upon activating the colored orthopedic casting materials of Examples 8-14 by dipping them in water, no significant leaching, migration, or bleeding of colorant from the resin was observed from any of Examples 8-14.

EXAMPLES 15-19

In these Examples 15-19, colored resins incorporating chromophore-containing polyols were prepared in accordance with the present invention.

In each of Examples 15-19, a colored, water curable, isocyanate functional, polyurethane prepolymer resin was prepared under dry conditions and constant agitation by adding the following chemical ingredients listed in Table III below, with each successive ingredient being added at about 5 minute intervals.

TABLE III

| Ingredient | Weight (g) |
| --- | --- |
| Isonate 2143L isocyanate (Dow Chemical) | 116 |
| Pluronic F-108 | 8 |
| Reactive colorants | See Table IV |
| Polyol mix | 76 (see Table V) |

As seen in Table III, various reactive colorants were added to each of Examples 15-19 in the amounts and ratios set forth in Table IV below.

TABLE IV

| Example | Reactive Colorant | Total Weight (g) | Resin Color Obtained |
| --- | --- | --- | --- |
| 15 | Reactints ® Red X52/Orange X38 (56/44 weight % ratio) | 0.6 | Red |
| 16 | Reactints ® Blue X3LV/Violet X80 (81/19 weight % ratio) | 0.7 | Blue |
| 17 | Reactints ® Blue X3LV/Violet X80 (76/24 weight % ratio) | 0.1 | Light Blue |
| 18 | Reactints ® Yellow X15/Blue X3LV (38/62 weight % ratio) | 0.4 | Green |
| 19 | Reactints ® Yellow X15/Orange X38 (99.5/0.5 weight % ratio) | 0.6 | Yellow |

As also seen in Table III above, in each of Examples 15-19, 76 grams of a polyol mix was employed. This polyol mix was obtained by adding together the ingredients listed in Table V below.

TABLE V

| Ingredient | Weight (g) |
| --- | --- |
| E-562 polyol (Union Carbide) | 660 |
| PPG 2025 polyol (Union Carbide) | 322.4 |
| LG 650 polyol (Union Carbide) | 204.6 |
| MEMPE catalyst | 38.0 |
| BHT | 15.8 |
| Dow Corning Antifoam 1400 (Dow Corning) (Formerly DB-100 silicone fluid) | 5.9 |

As can be seen from Table III, each of the colored resins produced in Examples 15-19 was produced by adding the reactive colorants after the isocyanate but before the uncolored polyols. Each of the 5 colored resins produced in Examples 15-19 was mixed and shaken for about 90 minutes to a uniform color, and then stored in an oven at about 120° F. (49° C.). After about 2 hours in the oven, it was observed that each colored resin still had uniform color, with no settling or separation of the colorants from the resins having been visually observed.

EXAMPLE 20

In this Example 20, a colored resin and colored orthopedic casting material incorporating chromophore-containing polyols were prepared in accordance with the present invention.

In this Example 20, a purple, water curable, isocyanate functional, polyurethane prepolymer resin was prepared under dry conditions and constant agitation by adding the following chemical ingredients listed in Table VI below, with each successive ingredient being added at about 5 minute intervals.

TABLE VI

| Ingredient | Weight (g) | Weight % | Equivalents |
| --- | --- | --- | --- |
| Isonate 2143L | 2081.60 | 56.09 | 14.46 |
| Pluronic F-108 | 148.00 | 3.99 | 0.02 |
| para-toluenesulfonyl chloride | 1.85 | 0.05 | 0.01 |
| Dow Corning Antifoam 1400 | 6.66 | 0.18 | 0 |
| BHT | 17.76 | 0.48 | 0.03 |
| MEMPE catalyst | 48.84 | 1.32 | 0.38 |
| PPG-425 polyol | 430.04 | 11.59 | 2.03 |
| PPG-725 polyol | 965.25 | 26.00 | 2.45 |
| Reactint ® Violet X80 | 5.55 | 0.15 | 0 |
| Reactint ® Red X52 | 5.55 | 0.15 | 0 |

The resultant purple colored resin was coated at a weight of about 40% onto a Scotchcast® 2 fiberglass scrim which had been abraded in accordance with the process set forth in FIG. 4 of U.S. patent application Ser. No. 07/376,873, filed on the same date as the present application, filed in the names of Matthew T. Scholz, Robert L. Assell, Ralph A. Wilkens, and Charles E. Alexson, under Express Mailing Certificate No. B75869812, and entitled "Orthopedic Casting Materials Having Superior Lamination Characteristics and Methods for Preparing Same", using a force of 450 newtons between the knurled roller and smooth roller. The abraded scrim had been rubbed over itself at a deflection of 6 millimeters according to the procedure outlined in FIGS. 4-5 of that same patent application.

EXAMPLES 21-28

In Examples 21-24 and 26-28, colored resins incorporating chromophore-containing polyols were prepared. Example 25 represents a control resin employing no colorant.

In each of Examples 21-28, a water curable, isocyanate functional, polyurethane prepolymer resin was prepared under dry conditions and constant agitation by adding the following chemical ingredients listed in Table VII below, with each successive ingredient being added at about 5 minute intervals.

TABLE VII

| Ingredient | Weight (g) | Weight (%) |
|---|---|---|
| Isonate 2143L | 1687.2 | 56.24 |
| Pluronic F-108 | 120.12 | 4.00 |
| Benzoyl chloride | 1.5 | 0.05 |
| Dow Corning Antifoam 1400 | 5.41 | 0.18 |
| BHT | 14.41 | 0.48 |
| MEMPE Catalyst | 39.64 | 1.32 |
| PPG-425 polyol | 363.97 | 12.13 |
| PPG-725 polyol | 758.74 | 25.29 |
| Reactint ® (see Tables VIII and IX) | 9.0 | 0.30 |

Each of the resultant resins was divided into 10 different samples, and each sample was placed in a 220 ml jar, sealed, and "aged" in an oven at 120° F. (49° C.). The samples of each example were kept in the 120° F. oven for different periods of time (corresponding to the number of days set forth in Tables VIII and IX), and were then removed from the oven and tested for viscosity. Upon removal from the oven, each sample of resin was placed in a 22° C. bath for a minimum of about 16 hours before testing. (This 16 hour "cool down" period was not included in the total "aging" time elapsed.) The viscosity of the sample was then measured using a Brookfield RVT Viscometer using spindles #6 and #7 at a speed of 10 rpm. The samples of Examples 25-28 were actually made and tested 6 days later than the samples of Examples 21-24.

The viscosities measured for each of Examples 21-24 is reported in Table VIII below, while the viscosities measured for each of Examples 25-28 is reported in Table IX below.

TABLE VIII

| | | Viscosity (centipoise) | | | | | |
|---|---|---|---|---|---|---|---|
| Example | Reactint ® Used | 1 Day in oven | 7 Days in oven | 12 Days in oven | 19 Days in oven | 26 Days in oven | 33 Days in oven |
| 21 | Orange X38 | 73000 | 76000 | 80000 | 87000 | 106000 | 126000 |
| 22 | Violet X80 | 73000 | 80000 | 80500 | 97000 | 122000* | 110000 |
| 23 | Black X40LV | 75000 | 74000 | 82000 | 97000 | 114000* | 120000 |
| 24 | Red X52 | 69500 | 72000 | 74000 | 91000 | 101000 | 112000 |

*Actually tested after 17 days (not 26 days) in the oven

TABLE IX

| | | Viscosity (centipoise) | | | | |
|---|---|---|---|---|---|---|
| Example | Reactint ® Used | 1 Day in oven | 6 Days in oven | 13 Days in oven | 20 Days in oven | 27 Days in oven |
| 25 | None (Control) | 68000 | 73000 | 86000 | 110000 | 109000 |
| 26 | Yellow X15 | 78000 | 87000 | 107000 | 127000 | 139000 |
| 27 | Blue X17AB | 82000 | 80000 | 97000 | 114000 | discarded due to discoloration |
| 28 | Blue X3LV | 77000 | 87000 | 110000 | 122000 | 133000 |

From Tables VIII and IX above, it is seen that the increase in viscosity over time of the various colored resins of Examples 21-24 and 26-28 was quite comparable to the increase in viscosity for Control Example 25. One exception to color stability in these Examples was Example 27 which discolored after about 27 days. Thus, although satisfactory results are achieved with Reactint ® Blue X3LV of Example 28, Reactint ® Blue X17AB of Example 27 would not be considered suitable for purposes of the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A colored orthopedic casting material, comprising:
   a flexible sheet; and
   a water curable resin coated onto said flexible sheet, said resin comprising an isocyanate functional, polyurethane prepolymer, said prepolymer being a liquid formed by the reaction of a polyol with an excess of a polyisocyanate, at least a portion of said polyol comprising a chromophore-containing polyol which becomes covalently bound into said prepolymer, said chromophore-containing polyol imparting a desired color to said resin-coated sheet;
   wherein said colored resin-coated sheet is stored in a moisture-free pouch until its desired usage, and
   wherein said colored resin-coated sheet is storage stable prior to such usage.

2. A colored orthopedic casting material as defined in claim 1 wherein said chromophore-containing polyol comprises a dyestuff bound to a polyether polyol.

3. A colored orthopedic casting material as defined in claim 1 wherein said chromophore-containing polyol is a Reactint ® polyol available from Milliken Research Corporation.

4. A colored orthopedic casting material as defined in claim 1 wherein said chromophore-containing polyol is a Reactint ® Black X40LV, Reactint ® Blue X3LV, Reactint ® Orange X38, Reactint ® Red X52, Reactint ® Violet X80, Reactint ® Yellow X15, or combinations of the foregoing.

5. A colored orthopedic casting material as defined in claim 1 wherein said colored resin-coated sheet is storage stable in that the uniformity of color in said colored resin-coated sheet remains substantially unchanged after about 5 weeks of aging at 120° F.

6. A colored orthopedic casting material as defined in claim 1 wherein said colored resin-coated sheet is storage stable in that the presence of said chromophore-containing polyol does not cause a significantly higher rate of viscosity increase in said resin over time as compared to a corresponding noncolored resin.

7. A colored orthopedic casting material as defined in claim 1 wherein the leaching or migration of color from said colored resin-coated sheet is substantially avoided.

8. A colored orthopedic casting material as defined in claim 1 wherein said chromophore-containing polyol is a liquid at room temperature.

9. A colored orthopedic casting material as defined in claim 1 wherein said chromophore-containing polyol comprises from about 0.01% to about 2% by weight of said resin.

10. A colored orthopedic casting material as defined in claim 1 wherein said resin further comprises a tertiary amine catalyst.

11. A colored orthopedic casting material as defined in claim 1 wherein said prepolymer resin has a viscosity of from about 10,000 to about 300,000 centipoise.

12. A colored orthopedic casting material as defined in claim 1 wherein said prepolymer resin has a viscosity of from about 10,000 to about 100,000 centipoise.

13. A colored orthopedic casting material as defined in claim 1 wherein said prepolymer resin has a viscosity of from about 10,000 to about 80,000 centipoise.

14. A colored orthopedic casting material as defined in claim 1 wherein the ratio of NCO groups in said polyisocyanate to OH groups in said polyol is between about 1.2 to 1 and about 4.5 to 1.

15. A colored orthopedic casting material as defined in claim 1 wherein the ratio of NCO groups in said polyisocyanate to OH groups in said polyol is between about 1.8 to 1 and about 3.8 to 1.

* * * * *

UNITED STATES PATENT AND TRADEMARK OFFICE
CERTIFICATE OF CORRECTION

PATENT NO. : 5,052,380
DATED : October 1, 1991
INVENTOR(S) : CHARLES C. POLTA

It is certified that error appears in the above-identified patent and that said Letters Patent is hereby corrected as shown below:

Abstract, line 1, "orthipedic" should be --orthopedic--.
Col. 1, line 53, "o" should be --to--.
Col. 15, Table VIII, last line, "17" should be --27--.
Col. 16, line 36, delete "a".

Signed and Sealed this

Fourteenth Day of June, 1994

BRUCE LEHMAN

Attest:

Attesting Officer

Commissioner of Patents and Trademarks